United States Patent [19]

Meltzer et al.

[11] Patent Number: 4,535,157
[45] Date of Patent: Aug. 13, 1985

[54] PROCESS FOR MAKING 6-DESOXY-6-METHYLENENALOXONE AND 6-DESOXY-6-METHYLENENALTREXONE

[75] Inventors: Peter C. Meltzer, Lexington; Jotham W. Coe, Belmont, both of Mass.

[73] Assignee: Key Pharmaceuticals, Inc., Miami, Fla.

[21] Appl. No.: 547,676

[22] Filed: Nov. 1, 1983

[51] Int. Cl.³ ............................................ C07D 489/08
[52] U.S. Cl. ......................................................... 546/44
[58] Field of Search ............................ 546/44, 46, 74

[56] References Cited

U.S. PATENT DOCUMENTS 3,814,768 6/1974 Fishman ................................. 546/46
4,322,426 3/1982 Hermann et al. ................... 424/260

OTHER PUBLICATIONS

Hahn, et al., J. Med. Chem., vol. 18, No. 3, pp. 259–262 (1975).

*Primary Examiner*—Donald G. Daus
*Assistant Examiner*—Diana G. Rivers

[57] ABSTRACT

An improved Wittig reaction for making 6-desoxy-6-methylenenaloxone and 6-desoxy-6-methylenenaltrexone from naloxone and naltrexone utilizing an alkoxide base in an ethereal solvent.

3 Claims, No Drawings

PROCESS FOR MAKING 6-DESOXY-6-METHYLENENALOXONE AND 6-DESOXY-6-METHYLENENALTREXONE

The present invention relates to an improved Wittig reaction for making 6-desoxy-6-methylenenaloxone and 6-desoxy-6-methylenenaltrexone (also called nalmefene) from naloxone and naltrexone, respectively.

Narcotic agonists such as morphine are commonly used to provide analgesia in cases of severe pain. As is well known, narcotic addiction and drug abuse are commonly associated with their use. Much effort has been directed to the development of satisfactory narcotic antagonists, drugs with the capacity to reverse or block the agonist effects of narcotics. Narcotic antagonists are presently used to reverse respiratory depression, a side effect when narcotics are administered, and are being tested as prophylactic agents in combating narcotic drug abuse. For the later purpose, a narcotic antagonist is required which exhibits little or no agonist properties, has an extended duration of action, and is preferably orally effective. Most narcotic antagonists synthesized thus far exhibit at least some degree of agonist activity.

The best known and currently utilized antagonists are naloxone and naltrexone; the later exhibits somewhat greater agonist activity but is of greater potency and has a longer duration of action. It has been discovered that the 6-desoxy derivatives of these compounds are even more useful as narcotic antagonists. Hahn and Fishman, *J. Med. Chem.*, Vol. 18, No. 3, pp. 259–262 (1975) describe the preparation and properties of 6-desoxy-6-methylenenaloxone and 6-desoxy-6-methylenenaltrexone. The compounds were prepared on a small scale from naloxone and naltrexone, respectively, using preformed methylenetriphenylphosphorane, prepared in situ from methyltriphenylphosphonium bromide, sodium hydride and dimethyl sulfoxide, as the reagent, according to the method of Corey and Chaykovsky, *J. Amer. Chem. Soc.*, 87, 1345, (1965).

The preparative process described by Hahn and Fishman requires complex temperature manipulations. For example, the dimsyl anion must be preformed at about 75°–80° C., the reaction mixture cooled to room temperature, and the methyltriphenylphosphonium bromide added, followed by adding of Nalberone then brought to 55°–60° C. for 18 hours, and cooled again for quenching. Attempts to scale up the Hahn and Fishman process, even on a modest scale, were unsuccessful.

We have discovered an improved process for the preparation of 6-desoxy-6-methylenenaloxone and 6-desoxy-6-methylenenaltrexone. Using an ethereal solvent and an alkoxide base to prepare the methylenetriphenylphosphorane reagent, only slightly in excess of three moles of methyl-triphenylphosphonium bromide is required, and not 60 moles as in the Hahn and Fishman process. Also, alkoxides are much easier and safer to handle than sodium hydride, making it feasible to carry out the reaction on a larger scale.

In general, the 6-desoxy-6-methylene derivatives are prepared, according to the invention, as follows: a vessel is charged with an alkoxide base, the alkali metal salt of a lower alcohol containing up to six carbon atoms, for example, potassium t-butoxide or potassium amylate and methyltriphenylphosphonium bromide. A lower-alkyl ether containing up to six carbon atoms such as tetrahydrofuran or diethyl ether, at 0°–60° C., preferably 20°–30° C., is introduced and the dispersion stirred. A solution of naloxone or naltrexone in the same ether at 0°–60° C., again preferably at about room temperature is added with stirring. After stirring for a period of time to allow the reaction to go to completion, the reaction mixture is quenched with water or aqueous ammonium chloride at 0°–50° C. and preferably 10°–20° C. Decomposition with aqueous ammonium chloride is preferred because it is the most convenient approach to bringing the reaction mixture to the appropriate pH prior to extraction; otherwise base, such as ammonium hydroxide, need be added to bring the pH to 8. The resultant 6-desoxy-6-methylene compound is extracted with an organic solvent such as chloroform, purified by passage over silica, and crystallized from a suitable solvent in yields of about 90% of the theoretical. The free base so obtained can be converted to its acid addition salts in the usual manner; for example, hydrogen chloride in a solvent such as diethyl ether, tetrahydrofuran, methylene chloride, chloroform, or ethyl acetate gives the corresponding hydrochloride.

Our invention is further illustrated by the following non-limiting example.

A dry, 2-liter, 3-neck, round bottom flask fitted with two stoppers and a magnetic stirring bar was charged with potassium t-butoxide (61.1 g, 0.545 mol) and methyltriphenylphosphonium bromide (194.4 g, 0.544 mol). Freshly distilled tetrahydrofuran (450 ml) was introduced at 20° C. The resultant thick, bright yellow dispersion was stirred at 20° C. for 0.5 h and further dry tetrahydrofuran (100 ml) was added. A solution of dry naltrexone (60.0 g, 0.176 mol) in dry tetrahydrofuran (200 ml) was then added dropwise over 40 min to the well-stirred dispersion maintained at 20° C.

In another run using a similar procedure but only 30 g of naltrexone, the reaction mixture was stirred for a further 1.25 h, then cooled to 10° C., and quenched with 20% aqueous ammonium chloride solution (75 ml) followed by water (100 ml). The organic layer was separated and the aqueous layer extracted with four 100 ml portions of chloroform. Solvent was evaporated from the tetrahydrofuran layer and the combined chloroform extracts, the residues combined and brought to pH 2 by addition of 2N hydrochloric acid. The resultant precipitate was filtered, washed with chloroform (4×100 ml) and suspended in a mixture of chloroform (500 ml) and water (250 ml). Ammonium hydroxide was added to attain a pH of 8 and the aqueous layer separated. The organic layer was dried over anhydrous sodium sulfate, filtered, and the solvent removed *in vacuo*. The resultant solid was dissolved in ethyl acetate (1400 ml), the solution filtered through a silica pad and the solvent evaporated. The product was recrystallized from chloroform and washed with hexane to yield pure 6-desoxy-6-methylenenaltrexone as a white solid. Yield: 27.0 g, 88%.

What is claimed is:

1. A method of preparing a 6-desoxy-methylene compound of the formula

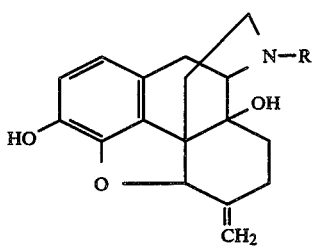

wherein R is CH₂CH=CH₂ or

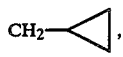, which comprises combining approximately equal molar amounts of potassium t-butoxide and methyltriphenylphosphonium formide to form a mixture and adding to that mixture tetrahydrofuran and stirring at about 20° C. for about 0.5 hours and then reacting with a compound of the formula

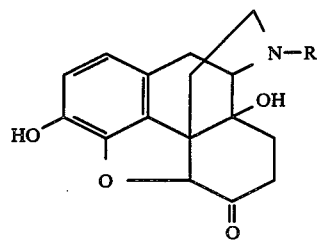

at about 20° C. for about 40 minutes and stirring for about 1.25 hours and decomposing the reaction mixture by the addition of water in the presence of ammonium chloride and recovering the resultant 6-desoxy-6-methylene compound.

2. A method according to claim 1 wherein R is CH₂CH=CH₂.

3. A method according to claim 1 wherein R is

.

* * * * *